United States Patent [19]

Reynolds

[11] Patent Number: 4,906,232
[45] Date of Patent: Mar. 6, 1990

[54] INTRAVASCULAR DELIVERY DEVICE

[75] Inventor: Gordon S. Reynolds, Bountiful, Utah

[73] Assignee: Abbott Laboratories, Abbott Park, Ill.

[21] Appl. No.: 162,476

[22] Filed: Mar. 1, 1988

[51] Int. Cl.[4] ............................................. A61M 5/00
[52] U.S. Cl. ................................... 604/171; 604/164; 604/159
[58] Field of Search ................. 604/40, 158, 159, 163, 604/164, 171, 263, 162

[56] References Cited

U.S. PATENT DOCUMENTS

| | | | |
|---|---|---|---|
| 3,796,211 | 3/1974 | Kohl | 604/171 |
| 3,894,540 | 7/1975 | Bonner, Jr. | 604/171 |
| 4,224,943 | 9/1980 | Johnson et al. | 604/164 |
| 4,235,232 | 11/1980 | Spaven et al. | 604/171 |
| 4,252,122 | 2/1981 | Halvorsen | 604/164 |
| 4,327,723 | 5/1982 | Frankhouser | 604/171 |
| 4,349,023 | 9/1982 | Gross | 604/164 |
| 4,419,094 | 12/1983 | Patel | 604/158 |
| 4,515,592 | 5/1985 | Frankhouser | 604/163 |
| 4,529,399 | 7/1985 | Groshong et al. | 604/53 |
| 4,551,137 | 11/1985 | Osborne | 604/171 |
| 4,613,329 | 9/1986 | Bodicky | 604/158 |
| 4,795,434 | 1/1989 | Kujawski | 604/164 |

OTHER PUBLICATIONS

"Arrow-Flex Percutaneous Sheath Introducer System with Cath-Gard", Arrow International, Inc., Reading, PA 19610, 1985.

Gehrich et al., "Optical Fluorescense and Its Application To An Intravascular Blood Gas Monitoring System", vol. BME-33, No. 2, pp. 117-132, Feb. 1986.

Primary Examiner—Stephen C. Pellegrino
Assistant Examiner—Ralph Lewis
Attorney, Agent, or Firm—Christensen, O'Connor, Johnson & Kindness

[57] ABSTRACT

An intravascular delivery device (10) for inserting and withdrawing a thin, elongate probe (12) through a catheter (14). The delivery device (10) includes a fitting (18) connected to a flexible guide tube (15) and a delivery assembly (20) comprising a fixed inner sleeve (22) and a slidable outer actuator sleeve (24). The fitting (18) has an internal axial bore into which a seal (28) is placed. The seal (28) has a cone-shaped forward end (31) and an internal axial bore through which the cable (11) slidably passes. The outer sleeve (24) has its proximal end (26) affixed to the larger cable insulation (17) that is joined to the sheath (16) of the cable (11). A first ring (38) affixed to the cable (11) and a second ring (40) affixed to the proximal end (36) of the inner strain relief sleeve (22) cooperate to limit movement of the outer actuator sleeve (24) as it is slid over the inner strain relief sleeve (22) away from the fitting (18). A side port (42) depends from the fitting (18) to allow fluid into and out of the guide tube (15) and the catheter (14). In addition, a contamination sleeve (62) may be fitted over the delivery assembly (20).

5 Claims, 3 Drawing Sheets

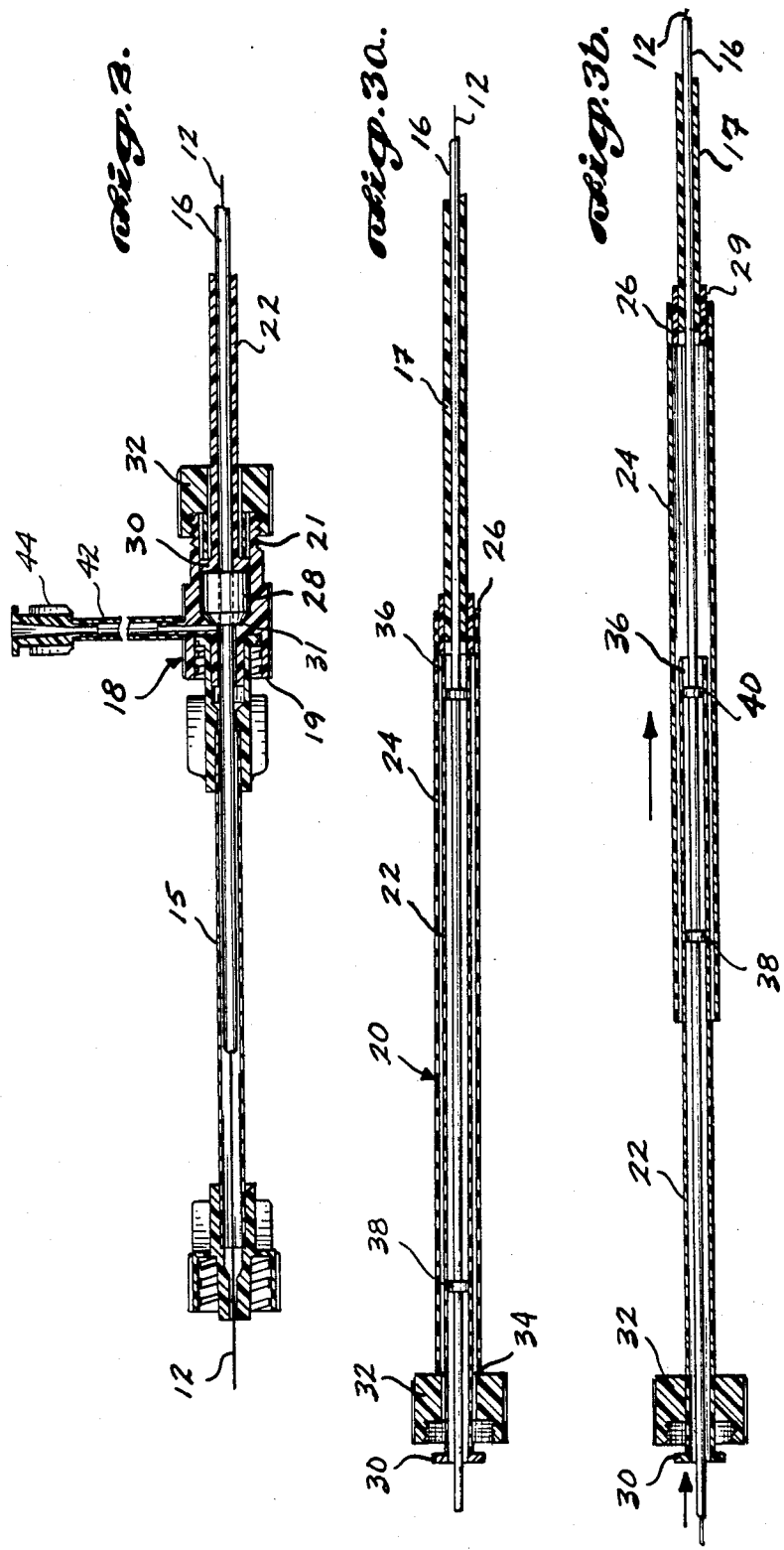

INTRAVASCULAR DELIVERY DEVICE

Technical Field

This invention pertains to delivery systems, and, more particularly, to an intravascular delivery device for inserting and withdrawing a thin, elongate probe through a catheter that has been injected into a blood vessel.

BACKGROUND OF THE INVENTION

The development of intravascular monitoring probes has created a need for a device that can be quickly and easily attached to a preplaced small gauge catheter and then operated to insert the probe through the catheter and into a blood vessel. Present methods and devices for inserting a catheter within a blood vessel are unsuitable for the delivery of probes for a number of reasons. First, these existing devices have no means to prevent the leakage of bodily fluids from the catheter as the probe is inserted into and withdrawn from the blood vessel. In addition, these prior art devices provide no secondary fluid path for pressure monitoring, blood sampling, or for the introduction of additional fluids into the artery. Furthermore, they do not provide means to center the probe within the catheter lumen while advancing the probe into the Blood vessel.

SUMMARY OF THE INVENTION

The present invention overcomes the foregoing and other disadvantages by providing an intravascular delivery device for inserting a thin, elongate probe through the bore of a small gauge catheter and into a blood vessel. The intravascular delivery device comprises a seal means having a guide tube attached at one end and a Probe delivery assembly attached to the other end, and a side port on the seal means in communication with the guide tube and the catheter. Preferably, the seal means is a fitting having an internal axial bore with a seal installed therein through which the probe passes. The side port is located upstream from the seal to permit fluid flow into and out of the guide tube. The Probe delivery assembly includes an inner sleeve having an axial bore through which the probe passes. The inner sleeve has one end affixed to the seal means. The delivery assembly further includes an outer sleeve having an internal axial bore sized to permit the outer sleeve to slide over the inner sleeve. The outer sleeve has one end attached to the probe so that sliding of the outer sleeve towards the fitting causes the probe to slide through the inner sleeve, through the seal means, and through the guide tube and catheter to enter into the blood vessel. The delivery assembly is further configured so that sliding of the outer sleeve away from the fitting causes the probe to be withdrawn from the blood vessel.

In accordance with another aspect of the invention, the delivery assembly includes a stop means to limit travel of the probe as the outer sleeve is slid away from the fitting. Preferably, the stop means comprises a first ring affixed to the probe and having an outside diameter sized so that it may be slid inside the inner sleeve. The stop means further includes a second ring formed on the inside of the inner sleeve and positioned downstream from the first ring so that as the probe and first ring move away from the fitting the first ring will contact the second ring and prevent further retraction of the probe.

As will be readily appreciated from the foregoing description, the intravascular delivery system allows placement of a sensing probe into a blood vessel through a preplaced small gauge catheter that also provides a secondary fluid path. The secondary fluid path is used for pressure monitoring, blood sampling, precalibration of sensors with read-out equipment or introduction of fluids into the bloodstream. In addition, fluid flow through the guide tube and catheter is used to assist in aligning the probe as it enters the catheter and advances into the blood vessel, thus preventing damage to the sensors at the probe tip that would result from misalignment by an operator hand feeding a sensor probe through a preplaced catheter.

BRIEF DESCRIPTION OF THE DRAWINGS

The foregoing and other advantages and features of the present invention will be better understood from the following description of the preferred embodiment of the invention when taken in conjunction with the following drawings, wherein:

FIG. 2 is an enlarged, partial view in cross section of the device illustrated in FIG. 1, showing the internal structure of the fitting;

FIG. 3a is an enlarged, partial view in cross section of the device illustrated in FIG. 1, showing the delivery assembly and the probe pushed through the inner sleeve;

FIG. 3b illustrates the probe in FIG. 3a withdrawn through the inner sleeve.

DETAILED DESCRIPTION OF THE PREFERRED EMBODIMENT

Figure 1:
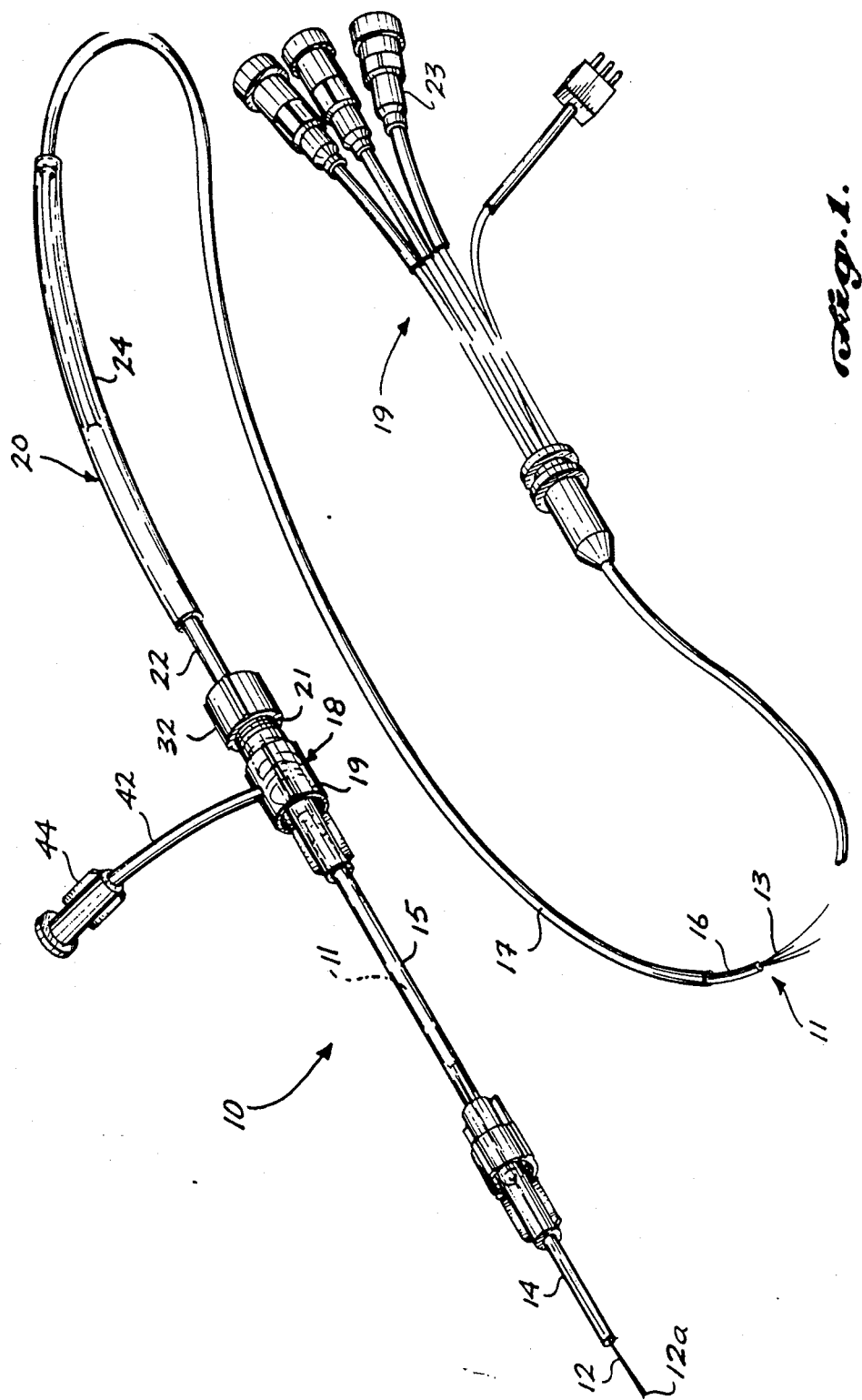
FIG. 1 is an isometric view of the intravascular delivery device formed in accordance with the present invention showing a probe inserted through a catheter.

The present invention as illustrated in FIG. 1 is directed to an intravascular delivery device 10 that inserts and withdraws a probe 12 through a catheter 14. The probe 12 generally is composed of cable 11 having one or more fiber optic strands or wires 13 with sensors 12a on the tips thereof for detecting the level of oxygen content and other parameters in the blood. Typically, such cables include a protective sheath 16 that encases the probe 12 and, as illustrated, may be further protected by an additional layer of insulation 17 to form a larger cable that terminates with connectors 23.

The intravascular delivery device 10 includes a bifurcated fitting 18 having a female end 19 connected to a flexible guide tube 15 that in turn is coupled to the catheter 14. The fitting 18 also has a male end 21 that is attached to a delivery assembly 20. The delivery assembly 20 is comprised of a fixed inner strain relief sleeve 22 and a slidable outer actuator sleeve 24. A side port 42 depends from the fitting 18 and is located upstream from a seal 28 (shown in FIG. 2) to allow the flow of fluids to and from the guide tube 15 and the catheter 14. A fitting 44 attaches the side port 42 to a fluid source or monitoring equipment. Preferably the guide tube 15 and the delivery assembly 20 are constructed of flexible PVC tubing while the seal 28 is formed from rubber, silicone or other material having similar properties.

As is more clearly shown in the cross-sectional illustration in FIG. 2, the fitting 18 has an internal axial bore into which the seal 28 is placed. The seal 28 itself has a cone-shaped forward end 31 and an internal axial bore through which the cable 11 slidably passes. The inner strain relief sleeve 22 has a flange 30 that is positioned inside the male end 21 of the fitting 18 and placed against the seal 28. A cap 32 is threadably received on the male end 21 of the fitting 18. As the cap 32 is threaded onto the fitting 18, it urges the flange 30 against the seal 28. This forces the seal 28 to compress the cone-shaped forward end 31 of the seal 28 inside the fitting 18. As a result the seal 28 will bear down evenly around the cable 11, thus creating a leak-proof seal. When the cap 32 is tightened to the correct tension, the seal 28 permits the cable 11 to slide through it with minimum resistance while preventing the back flow of fluid from the catheter 14 and the flexible guide tube 15. Further tightening of the cap 32 causes the seal 28 to bear heavily on the cable 11, thereby firmly locking the cable 11 in place within the fitting 18.

FIGS. 3a and 3b illustrate in greater detail the structure and function of the delivery assembly 20. The outer actuator sleeve 24 has a proximal end 26 and a distal end 34. Attached at the proximal end 26 is the larger cable insulation 17 that is joined to the cable sheath 16. A suitably sized collar 29 is used to affix the insulation 17 to the proximal end 26 of the outer actuator sleeve 24. Located near the center of and affixed to the sheath 16 of the cable 11 is a first ring 38. The outside diameter of the first ring 38 is sized to permit it to slide within the inner strain relief sleeve 22 as the cable 11 is moved back and forth by the outer actuator sleeve 24. A second ring 40 is formed inside the proximal end 36 of the inner sleeve 22. The second ring 40 has an internal axial bore that permits the cable 11 to slide therethrough.

FIG. 3a illustrates the position of the outer sleeve 24 when the cable 11 is fully advanced through the inner strain relief sleeve 22. In this configuration, the distal end 34 of the outer actuator sleeve 24 will contact the cap 32, preventing further advancement of the cable 11. With the outer sleeve 24 formed at the correct length, the distal end 34 will contact the cap 32 at the same time as or, preferably, before the cable insulation 17 and the collar 29 contact the proximal end 36 of the inner strain relief sleeve 22. This embodiment provides a visible indication that the probe 12 is fully advanced through the catheter 14.

In FIG. 3b, the outer sleeve 24 is slid away from the cap 32. As the outer sleeve 24 moves the probe through the inner strain relief sleeve 22, the first ring 38 will slide through the inner strain relief sleeve 22 until it contacts the second ring 40, thus preventing further movement of the outer actuator sleeve 24 away from the cap 32. The first and second rings prevent the total removal of the outer sleeve 24 from slidable engagement with the inner strain relief sleeve 22 which could result in withdrawal of the cable 11 from the packing seal 28, thus allowing a loss of body fluids through the fitting 18.

Figure 4:
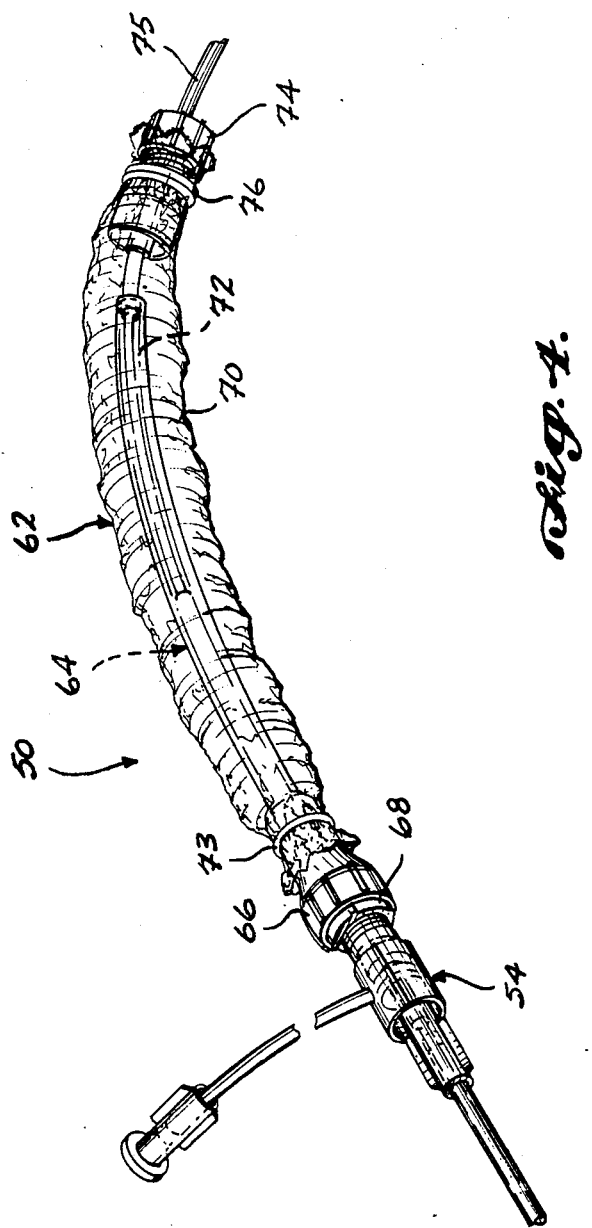
FIG. 4 is an isometric view of a delivery device protected by a contamination sleeve.

FIG. 4 illustrates an alternative embodiment wherein the intravascular delivery device 50 further includes a contamination sleeve 62 placed over the delivery assembly 64 to prevent bacteria and other outside contaminants from entering the bloodstream. The contamination sleeve 62 includes a flexible boot 66 fitted over the cap 68 of the fitting 54, a longitudinally collapsible tube 70 attached to the flexible boot 66 by an elastic O-ring 73, and a clamp fitting 74 that extends past the outer sleeve 72 and is attached to the probe insulation 75. The tube 70 is affixed to the clamp fitting 74 by one or more elastic O-rings 76. As will be readily appreciated from the foregoing description, the intravascular delivery device provides a method and apparatus for placement of a sensing probe into a blood vessel through a pre-placed small gauge catheter. The present invention allows a probe to be repeatedly inserted and withdrawn from the bloodstream without the loss of bodily fluids. In addition, the device includes a side port attachment that permits a secondary fluid path that may be used for pressure monitoring, blood sampling, or introduction of fluids into the bloodstream. In addition, fluid flow in the catheter may be used to assist in aligning the probe as it is advanced passed a hub on the catheter and into the blood vessel, thus preventing damage to the sensitive probe tips that would otherwise result from scraping of the sides of the catheter. Furthermore, the collapsible protection sleeve protects the patient from contamination of the blood vessel through the sliding sleeves in the delivery assembly. In addition, the device may be constructed of inexpensive and lightweight plastic materials that allow it to be disposed after use.

Although the present invention has been described in its application to the health care field, it is to be understood that the intravascular delivery device will be useful in other areas where a small diameter elongate object is to be repeatedly inserted into and withdrawn from a fluid-filled member.

While a preferred embodiment of the invention has been illustrated and described, it will be appreciated that various changes can be made therein without departing from the spirit and scope of the invention. Consequently, the invention can be practiced otherwise than as specifically described herein.

The embodiments of the invention in which an exclusive property or privilege is claimed are defined as follows:

1. An intravascular delivery device for inserting a thin, elongate probe through a catheter having an internal axial bore and into a blood vessel, the device comprising:
 (a) seal means to prevent leakage of body fluids from the device while permitting passage of the probe through the catheter; and
 (b) a delivery assembly attached to said seal means, the delivery assembly including:
  (i) an inner sleeve having an axial bore through which the probe passes, said inner sleeve having one end attached to said seal means;
  (ii) an outer actuator sleeve having an internal axial bore sized to permit said outer sleeve to slide over said inner sleeve, said outer sleeve having one end attached to the probe so that sliding of said outer sleeve toward said seal means causes the probe to slide through said inner sleeve, through said seal means, and advance the probe through the catheter to enter into the blood vessel, and, further, so that sliding of said outer sleeve away from said seal means causes the probe to be withdrawn from the blood vessel;
 (c) a side port on said seal means in communication with the internal axial bore of the catheter to permit fluid flow into and out of the catheter; and
 (d) stop means to limit travel of the probe as said outer actuator sleeve is slid away from said seal means, said stop means comprising a first ring fixedly mounted to the probe, said first ring having an outside diameter size to permit said ring to slide within said inner sleeve, and a second ring fixedly mounted to the inside of said inner sleeve and positioned on one side of said first ring so that as said outer sleeve moves away from said fitting, said first ring slides on the inside of said inner sleeve away from said fitting to come into contact with said second ring to thereby stop the travel of said outer sleeve and the probe.

2. The device of claim 1, wherein said delivery assembly further includes a longitudinally collapsible contamination sleeve placed around said inner sleeve and said outer sleeve to prevent contamination of the body fluids.

3. The device of claim 1, further comprising a flexible guide tube connected at one end to said seal means and at the other end to the catheter.

4. The device of claim 1, wherein said seal means comprises a fitting having an internal axial bore for slidably receiving the probe, and a seal installed therein through which the probe slides.

5. The device of claim 1, wherein said fitting includes a cap slidably received thereon for adjustably tightening the seal around the probe to thereby increase and decrease the tension exerted on the probe by the seal.

* * * * *

UNITED STATES PATENT AND TRADEMARK OFFICE
CERTIFICATE OF CORRECTION

PATENT NO. : 4,906,232
DATED : March 6, 1990
INVENTOR(S) : G.S. Reynolds

It is certified that error appears in the above-identified patent and that said Letters Patent is hereby corrected as shown below:

| Column | Line | |
|---|---|---|
| [57] | 19 | after "fluid" insert --flow-- |
| 1 | 27 | "Blood" should be --blood-- |
| 1 | 37 | "Probe" should be --probe-- |
| 1 | 43 | "Probe" should be --probe-- |
| 3 | 18 | "3aand" should be --3a and-- |
| 4 | 40 | "the probe" should be --a probe-- |
| 4 | 40 | "the probe" should be --a probe-- |
| 4 | 41 | "the catheter" should be --a catheter, said seal means having a distal end for attachment to the catheter and a proximal end;-- |
| 4 | 45 | "the probe" should be --said probe-- |
| 4 | 46 | "one end" should be --a distal end-- |
| 4 | 46 | after "said" insert --proximal end of said-- |
| 4 | 50 | "one end" should be --a proximal end-- |
| 4 | 50 | "the probe" should be --said probe-- |
| 4 | 52 | "the probe" should be --said probe-- |

UNITED STATES PATENT AND TRADEMARK OFFICE
CERTIFICATE OF CORRECTION

PATENT NO. : 4,906,232
DATED : March 6, 1990
INVENTOR(S) : G.S. Reynolds It is certified that error appears in the above-identified patent and that said Letters Patent is hereby corrected as shown below:

| Column | Line | |
|---|---|---|
| 4 | 53 | "the probe" should be --said probe-- |
| 4 | 56 & 57 | "the probe" should be --said probe-- |
| 4 | 61 | "the probe" should be --said probe-- |
| 4 | 64 | "the probe" should be --said probe-- |
| 4 | 65 | "size" should be --sized-- |
| 4 | 68 | "on one side of" should be --proximal to-- |
| 5 | 5 | "the probe" should be --said probe-- |

Signed and Sealed this

Twenty-ninth Day of October, 1991

Attest:

HARRY F. MANBECK, JR.

*Attesting Officer*     *Commissioner of Patents and Trademarks*